United States Patent [19]

Bouisset et al.

[11] 4,377,533

[45] Mar. 22, 1983

[54] PROCESS FOR INTRODUCING ALKYL RADICALS INTO CARBON CHAINS HAVING A FUNCTIONAL GROUP AND COMPOUNDS PREPARED BY SAID PROCESS

[75] Inventors: Michel Bouisset; Michel Chignac, both of Sisteron; Claude Grain, Volonne; Charles Pigerol, Saint-Ouen, all of France

[73] Assignee: Sanofi, Paris, France

[21] Appl. No.: 250,852

[22] Filed: Apr. 3, 1981

Related U.S. Application Data

[63] Continuation-in-part of Ser. No. 209,895, Nov. 24, 1980, abandoned.

[30] Foreign Application Priority Data

Dec. 7, 1979 [FR] France .................................. 79 30039

[51] Int. Cl.³ .................. C07C 120/00; C07C 121/16
[52] U.S. Cl. ............................. 260/465.1; 260/465 R; 260/465.9; 260/464; 560/231; 560/236; 562/606; 564/215
[58] Field of Search ................ 260/465.1, 465 R, 464; 560/236; 562/606; 564/215

[56] References Cited

U.S. PATENT DOCUMENTS

| | | | |
|---|---|---|---|
| 3,936,490 | 2/1976 | Hofmann et al. | 562/606 X |
| 4,127,604 | 11/1978 | Chignac et al. | 260/465.1 X |
| 4,155,929 | 5/1979 | Chignac et al. | 260/465.1 |

FOREIGN PATENT DOCUMENTS

| | | |
|---|---|---|
| 980279 | 1/1965 | United Kingdom . |
| 1467739 | 3/1977 | United Kingdom . |
| 1522450 | 8/1978 | United Kingdom . |
| 1529786 | 10/1978 | United Kingdom . |

OTHER PUBLICATIONS

C.A., 2945f, (1969), vol. 70, Caubere et al.
C.A., 87770w (1971), vol. 75, Caubere et al.
C.A., 119288n (1974), vol. 81, Caubere et al.
Fieser et al., Reagents for Organic Synthesis, vol. 1, (1967), John Wiley & Sons, pp. 907, 908, 1038.

*Primary Examiner*—Joseph Paul Brust
*Attorney, Agent, or Firm*—Mason, Kolehmainen, Rathburn & Wyss

[57] ABSTRACT

Process for introducing a substituent selected from branched- or straight-chain alkyl radicals having from 1 to 12 carbon atoms, aralkyl or cycloalkyl radicals in which the alkyl moiety has from 1 to 4 carbon atoms, into a carbon chain bearing a stable functional group the said carbon chain having at least one proton in α-position in relation to this functional group, process whereby, in a first step, this carbon chain is reacted with a complex base comprising a mixture of alkali metal amide and alkali metal alcoholate suspended in an anhydrous organic solvent to provide temporarily a carbanion, then in a second step this carbanion is reacted in an anhydrous organic solvent with an alkyl, aralkyl or cycloalkyl halide corresponding to the substituent to be introduced.

8 Claims, No Drawings

PROCESS FOR INTRODUCING ALKYL RADICALS INTO CARBON CHAINS HAVING A FUNCTIONAL GROUP AND COMPOUNDS PREPARED BY SAID PROCESS

This application is a continuation-in-part of our prior application Ser. No. 209,895, filed Nov. 24, 1980, now abandoned.

This invention relates to a novel process of alkylation i.e. a process for introducing substituents into a carbon chain these substituents being straight- or branched-chain alkyl radicals and aralkyl and cycloalkyl groups.

More particularly, the invention provides a process for introducing, by a substitution reaction into a carbon chain bearing a functional group and having at least one proton in α-position in relation to this functional group, at least one group selected from straight- or branched-chain alkyl radicals having from 1 to 12 carbon atoms, aralkyl radicals, such as benzyl, and cycloalkyl radicals, such as cyclohexyl, the alkyl moiety having from 1 to 4 carbon atoms.

The aforesaid functional group can be for instance a nitrile radical, a carboxylic acid radical, free or esterified by a straight- or branched-chain alkyl radical having from 1 to 5 carbon atoms, or a tertiary amide radical of general formula:

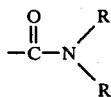

in which R represents a straight-chain alkyl radical having from 1 to 3 carbon atoms.

Thus, the invention relates to a process for preparing compounds of the general formula:

      I in which $R_1$ represents hydrogen or a straight- or branched-chain alkyl radical having from 1 to 6 carbon atoms, $R_2$ represents a straight- or branched-chain alkyl radical having from 1 to 12 carbon atoms, an aralkyl radical such as benzyl or a cycloalkyl radical such as cyclohexyl, $R_3$ represents hydrogen or the radicals as defined for $R_2$ above and Z represents a stable functional group as presented above, the said compounds being obtained from a carbon chain of the general formula:

      II in which $R_1$ and Z have the same meaning as defined above.

In particular, the invention relates to a process for preparing compounds of formula I in which Z represents a nitrile or carboxylic group and in which at least two of the radicals $R_1$, $R_2$ and $R_3$ represent an n-propyl radical namely more particularly di-n-propylacetic acid, di-n-propylacetonitrile and tri-n-propylacetonitrile.

These last-cited compounds are well known together with their process of preparation.

Thus, di-n-propylacetic acid and alkali metal salts thereof are described in U.K. Specification No. 980,279. They are widely used for their neurotropic properties and more particularly for their anticonvulsant properties. The sodium salt thereof is one of the most valuable anti-epileptic agents now on the market and is also used in the treatment of personality and behaviour disturbances linked to epilepsy.

Presently, the most conventional and most widely used process for preparing di-n-propylacetic acid is described in U.K. Specification No. 1,529,786. This process consists in treating diethylmalonate under pressure and in a methanolic medium first with sodium methylate and then with allyl chloride in accordance with working conditions well defined for each step. The diethyl diallylmalonate is then saponified with sodium hydroxide and the salt so formed is acidified to give diallylmalonic acid which is decarboxylated by heating to diallylacetic acid, which is itself subsequently hydrogenated on palladium charcoal to give di-n-propylacetic acid. This process presents a disadvantage in that it comprises a relatively high number of steps in which the operating conditions which have to be respected cause difficulties of a technical nature.

Moreover, undesirable reactions may cause the formation of impurities, for example 2-allyl-valerolactone concurrently with diallyl malonic acid, which must be eliminated. These inconveniences have an unfavourable influence on the yield and the cost-price of the final product. Similarly, di-n-propylacetonitrile is also known, this compound being useful for preparing di-n-propylacetamide which possesses very valuable neuropsychotropic properties as is also indicated in U.K. Specification No. 980,279.

The preparation of this nitrile is also described in U.K. Specification No. 1,522,450 involving the use of complicated procedures and dangerous reagents such as sodium cyanide.

Finally, tri-n-propylacetonitrile is also known and utilized for preparing methylamine derivatives possessing valuable pharmacological properties. Thus, tri-n-propylmethylamine is valuable for treating Parkinson's disease and for correcting extra-pyramidal disturbances provoked by neuroleptics as is described in U.K. Specification No. 1,467,739. When classical processes for the preparation of trialkylacetonitriles are used for preparing tri-n-propylacetonitrile by alkylating the α-position of aliphatic nitriles, mixtures of nitriles mono-, di- and tri-substituted in the α-position are obtained as well as undesirable products resulting from the reaction of the alkyl halides and the nitriles. The yield and the purity of the desired product are thus unsatisfactory. Furthermore, the purification of this nitrile by fractional distillation of the said mixture is difficult and also lowers the yield.

The process of the invention does not present the disadvantages cited above. It constitutes an improvement on the processes of the prior art since it is more simple, the number of steps required being less. Therefore, the cost of such a process will be lowered.

The process of the invention consists, for the introduction, into a carbon chain of formula II above i.e. a chain bearing a functional group and having at least one proton in the α-position in relation to this functional group, of at least one substituent selected from alkyl radicals having from 1 to 12 carbon atoms, aralkyl radicals and cycloalkyl radicals in which the alkyl moiety has from 1 to 4 carbon atoms:

in a first step
in reacting this carbon chain with a complex base comprising a mixture of alkali metal amide and alkali metal alcoholate to provide temporarily a carbanion,
then, in a second step
in reacting this carbanion with an alkyl halide of the general formula:

$$R_2X \text{ or } R_3X$$

in which X represents a halogen atom, preferably chlorine or bromine, and $R_2$ and $R_3$ represents a straight- or branched-chain alkyl radical having from 1 to 12 carbon atoms, an aralkyl radical such as benzyl or a cycloalkyl radical such as cyclohexyl.

When it is desired to introduce two such substituting groups into the carbon chain of formula II, the same two steps are repeated for the second substituent, the alkyl halide used in the second step corresponding, in the two successive pairs of steps, to the two groups to be introduced.

When these two groups are identical, the final product can be obtained in one operation by introducing an excess of the single alkyl halide used for performing the two substitutions.

The process of the invention can be illustrated by the following reaction schema:

$$R_1-CH_2-Z \xrightarrow[(1)]{BH} R_1-\overset{\ominus}{CH}-Z \xrightarrow[(2)]{R_2X} R_1-\underset{}{\overset{R_2}{\underset{}{CH}}}-Z$$
$$\text{II} \quad\quad\quad\quad \text{III} \quad\quad\quad\quad \text{IV}$$

$$(3) \Big\downarrow B'H$$

$$V \quad R_1-\underset{}{\overset{R_2}{\underset{}{\overset{\ominus}{C}}}}-Z$$

$$(4) \Big\downarrow R_3X$$

$$I \quad R_1-\underset{R_3}{\overset{R_2}{C}}-Z$$

It is clear that for each pair of steps (1)-(2) and (3)-(4), the mechanism of action is identical and that each pair can be undertaken independently of each other i.e.:
  to obtain a compound of formula IV from a compound of formula II
  to obtain a compound of formula I from a compound of formula IV or successively i.e.:
  to obtain a compound of formula I from a compound of formula II, the complex bases BH and B'H being optionally the same or different in this case
or finally, in the form of a single pair which occurs twice and can be represented as follows. In this case, $R_2$ and $R_3$ have the meaning of $R_1$:

$$R_1-CH_2-Z \xrightarrow[(1)]{BH} R_1-\overset{\ominus}{CH}-Z \xrightarrow[(2)]{R_1X} \underset{R_1}{\overset{R_1}{\diagdown}}CH-Z \quad IV'$$
$$\text{II} \quad\quad\quad \text{III}$$

$$(3') \Big\downarrow BH$$

$$R_1-\underset{R_1}{\overset{R_1}{C}}-Z \xleftarrow[(4')]{R_1X} \underset{R_1}{\overset{R_1}{\diagdown}}\overset{\ominus}{C}-Z$$
$$\text{I'} \quad\quad\quad\quad\quad \text{V'}$$

The steps (3') and (4') are identical to steps (1) and (2) respectively, using the same reagents to provide a compound of formula I' in which the three alkyl substituents are identical.

Such a case corresponds to the direct preparation of a trialkyl derivative, for example tri-n-propylacetonitrile, as exemplified below. The mixtures referred to here as "BH" and which are called "complex bases" are those which can be represented by the symbolic formula:

$$MNR_4/R_5OM'$$

in which $R_4$ represents $H_2(C_2H_5)_2$ or $(iso-C_3H_7)_2 \cdot R_5$ represents a straight- or branched-chain alkyl radical having from 1 to 7 carbon atoms or a radical $C_2H_5-O-CH_2-CH_2-$ or $CH_3-O-CH_2-CH_2-$ and M and M', which are the same or different, represent an alkali metal such as lithium, sodium or potassium.

Such mixtures of an alkali metal alcoholate and alkali metal amide dissolved or suspended in a solvent such as tetrahydrofuran were prepared and studied for the first time, some ten years ago, by P. CAUBERE et al in Bull. Soc. Chim. France, 1969 p. 2483-2489. These mixtures were found to possess very marked basic properties.

The authors cited above studied more particularly the application of such complex bases to alkylations (Bull. Soc. Chim. France 1971, p. 2334-2338) and summarized their work on this subject in "Topics in Current Chemistry" 73, Springer-New-York, 1978 p. 49-103.

From this summary it can be seen that, although the preparation of carbanions and their alkylation by means of a base complex constitutes a reaction of general character, no attempt has ever been made to apply this reaction to the preparation of carbanions derived from chains containing functional groups as defined by formula I above.

The present invention which involves this application, represents a very marked technical progress since the process for obtaining the required compounds can be simplified and can provide purer compounds with very high yields.

The complex base can be obtained by slowly adding a solution of 0.7 mol of an alcohol or of a solid alkali metal alcoholate in tetrahydrofuran to a suspension of 1.4 to 5.6 mols of alkali metal amide in an anhydrous organic solvent such as tetrahydrofuran, benzene, a tetrahydrofuran/isopropyl ether mixture or a tetrahydrofuran/benzene mixture. The reaction is exothermic but the temperature can be controlled between 25° and 55° C. for 1 to 2 hours.

The process of the invention i.e. each pair of reactions (1)-(2) and/or (3)-(4) or (3')-(4'), consists in slowly introducing, while stirring, in complex base into a mixture comprising 1 mol of starting compound of formula II or IV and 1 mol of alkyl halide of formula $R_2X$ or $R_3X$ respectively, dissolved in an anhydrous organic solvent such as one of those previously cited, at a temperature of 0° to 72° C., preferably from 10° to 20° C. The mixture is maintained at this temperature and under stirring for 30 min. to 120 min. after the complex base is completely added. The process of the invention can also be performed by reversing the order of introduction of the reagents namely by introducing the solution of compounds of formula II or IV and of alkyl halide of formulae R₂X or R₃X into the suspension of complex base, at a temperature of −10° to 20° C.

When the reaction is terminated, the reaction mixture is hydrolysed at a temperature between −10° and +10° C. to form, after neutralisation or acidification according to the Z function, the compound of formula I or I' which is collected after extraction.

The following Examples give a non-limitative illustration of the process of the invention.

It is evident that the invention also relates to the compounds represented by the general formula:

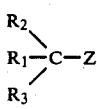

in which:

Z represents a functional group selected from a nitrile radical, a carboxylic acid radical free or esterified by a straight- or branched-chain alkyl radical having from 1 to 5 carbon atoms, a tertiary amide radical of general formula:

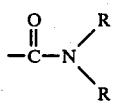

in which R represents a straight-chain alkyl radical having from 1 to 3 carbon atoms $R_1$ represents hydrogen or a straight- or branched-chain alkyl radical having from 1 to 6 carbon atoms $R_2$ represents a branched- or straight-chain alkyl radical having from 1 to 12 carbon atoms, an aralkyl radical or a cycloalkyl radical in which the alkyl moiety has from 1 to 4 carbon atoms and $R_3$ represents hydrogen or the radicals as defined for $R_2$ above whenever such compounds are prepared in accordance with the above-described process of the invention.

EXAMPLE 1

Preparation of di-n-propylacetonitrile from valeronitrile (a) Preparation of the complex base sodium amide/sodium t-butylate in a 2:1 ratio Into a 0.5-1 flask fitted with a stirrer, a thermometer, an isobaric dropping-funnel with a nitrogen inlet and a condenser with a calcium chloride trap, were introduced 150 ml of isopropyl ether and 100 ml of tetrahydrofuran. Nitrogen was then passed through and 81.9 g (2.1 mols) of sodium amide in powder were added.

Into this medium, a solution of 51.8 g (0.7 mol) of t-butanol in 50 ml of tetrahydrofuran was then introduced dropwise, under nitrogen atmosphere and at room-temperature. The temperature of the reaction medium rose to 45°-50° C. and this same temperature was kept constant until the operation of addition of t-butanol was terminated.

Stirring of the medium was maintained for a further 90 min. at 45°-50° C. and then the medium was cooled to 20° C.

(b) Formation of the valeronitrile carbanion and alkylation with n-propyl bromide Into a 1-1 flask fitted with a mechanical stirrer, a thermometer, a condenser with a calcium chloride trap and an isobaric dropping-funnel itself fitted with a stirrer and a nitrogen inlet, were introduced 83 g (1 mol) of valeronitrile, 123 g (1 mol) of n-propyl bromide and 350 ml of isopropyl ether.

The mixture of complex base was placed in the dropping-funnel and the flask was rinsed twice with 25 ml of tetrahydrofuran. The reaction medium was placed under nitrogen atmosphere and the mixture of complex base was stirred.

The mixture in the flask was cooled to 12±1° C. and then the mixture of complex base was added by fractions the temperature being maintained between 9° and 18° C. The operation of introduction lasted 60 to 90 minutes. Stirring was maintained a further 60 minutes between 10° and 15° C. and then the mixture was cooled to 0°-5° C.

The dropping-funnel which had contained the complex base was replaced by an identical dropping-funnel containing 100-125 ml of water under nitrogen atmosphere. The reaction medium was slowly hydrolysed at a temperature below 10° C. The mixture was transferred into a decantation funnel.

The aqueous phase was decanted and the organic phase was washed twice with 125 ml of water, twice with 125 ml of 10%-hydrochloric acid and twice with 125 ml of water. The organic phase was dried on sodium sulphate and the solvents were eliminated under atmospheric pressure.

In this manner, di-n-propylacetonitrile was obtained in a yield of 81.3%.

EXAMPLE 2

Preparation of di-n-propylacetonitrile from valeronitrile (a) Preparation of the complex base sodium amide/sodium isopropylate in a 2:1 ratio The method described in paragraph (a) of Example 1 above was employed using 16.4 g (0.42 mol) of sodium amide, 8.4 g (0.14 mol) of isopropanol, in 40 ml of isopropyl ether and 20 ml of tetrahydrofuran.

(b) Formation of the carbanion of valeronitrile and alkylation with n-propyl bromide The method described in paragraph (b) of Example 1 above was employed using a mixture of 16.6 g (0.2 mol) of valeronitrile and 24.6 g (0.2 mol) of n-propyl bromide in 60 ml of isopropyl ether.

The mixture of complex base was introduced into this medium and the dropping-funnel was rinsed with 10 ml of tetrahydrofuran. The operation of introduction lasted 1 hour at a temperature between 10° and 15° C. After this operation was terminated, the mixture was maintained at 15° C. The reaction product was treated and isolated in the same manner as that described in paragraph (b) of Example 1. After that, the solvent was evaporated off.

In this manner, di-n-propylacetonitrile was obtained in a yield of 62.5%.

EXAMPLE 3

Preparation of di-n-propylacetonitrile from valeronitrile (a) Preparation of the complex base sodium amide/sodium n-propylate in a 2:1 ratio The method of paragraph (a) of Example 2 above was employed with the same quantities but using n-propanol in place of isopropanol.

(b) Formation of the carbanion of valeronitrile and alkylation with n-propyl bromide The method of paragraph (b) of Example 2 was employed.

In this manner, di-n-propylacetonitrile was obtained in a yield of 68.9%.

EXAMPLE 4

Preparation of di-n-propylacetonitrile from valeronitrile (a) Preparation of the complex base sodium amide/sodium 2-ethoxy-ethylate The method of paragraph (a) of Example 2 above was employed but using 12.6 g (0.14 mol) of 2-ethoxyethanol in place of isopropanol.

(b) Formation of the carbanion of valeronitrile and alkylation with n-propyl bromide The method of paragraph (b) of Example 2 was employed, adding the complex base in 2 hours between 5° and 10° C. and maintaining the mixture for 1 hour between 10° and 15° C. after the operation of addition was terminated.

In this manner, di-n-propylacetonitrile in a yield of 75.4% was obtained.

EXAMPLE 5

Preparation of di-n-propylacetonitrile from valeronitrile (a) Preparation of the complex base sodium amide/sodium t-butylate in a 3:1 ratio The method of paragraph (a) of Example 2 above was employed but using 21.84 g (0.56 mol) of sodium amide and 12.3 g (0.14 mol) of t-amyl alcohol.

(b) Formation of the carbanion of valeronitrile and alkylation with n-propyl bromide The method of paragraph (b) of Example 2 was employed using the same quantities.

In this manner, di-n-propylacetonitrile was obtained in a yield of 59.1%.

EXAMPLE 6

Preparation of di-n-propylacetonitrile from valeronitrile (a) Preparation of the complex base sodium amide/sodium t-amylate in a 5:1 ratio The method of paragraph (a) of Example 2 above was employed but using 32.76 g (0.84 mol) of sodium amide and 12.3 g (0.14 mol) of t-amyl alcohol.

(b) Formation of the carbanion of valeronitrile and alkylation with n-propyl bromide The method of paragraph (b) of Example 2 was employed using the same quantities of valeronitrile and n-propyl bromide but maintaining the temperature between 0° and 3° C. while the complex base was being added.

In this manner, di-n-propylacetonitrile was obtained in a yield of 25.1%.

EXAMPLE 7

Preparation of di-n-propylacetonitrile from valeronitrile (a) Preparation of the complex base sodium amide/potassium t-butylate in a 2:1 ratio The method of paragraph (a) of Example 2 was employed but using 10.92 g (0.28 mol) of sodium amide and 15.7 g (0.14 mol) of potassium t-butylate in 45 ml of tetrahydrofuran.

(b) Formation of the carbanion of valeronitrile and alkylation with n-propyl bromide The method of paragraph (b) of Example 2 was employed using the same quantities of valeronitrile and n-propyl bromide but with 55 ml of tetrahydrofuran as diluent.

In this manner, di-n-propylacetonitrile was obtained in a yield of 42.5%.

EXAMPLE 8

Preparation of di-n-propylacetonitrile from valeronitrile (a) Preparation of the complex base lithium amide/potassium t-butylate in a 2:1 ratio Into 200 ml of liquid ammonia, 0.97 g (0.14 mol) of lithium was introduced at a temperature between $-40°$ and $-45°$ C. and the mixture was maintained under stirring for 8 hours.

The liquid ammonia was eliminated and 7.9 g (0.07 mol) of potassium t-butylate in 35 ml of tetrahydrofuran were introduced. While stirring the mixture was heated for 2 hours at 55° C.

(b) Formation of the carbanion of valeronitrile and alkylation with n-propyl bromide The mixture prepared in paragraph (a) hereabove was cooled to 15° C. and a solution of 8.3 g (0.1 mol) of valeronitrile and 12.3 g (0.1 mol) of n-propyl bromide in 30 ml of tetrahydrofuran was added.

The operation of addition lasted 1 hour at a temperature of 15° C. and the mixture was maintained at this temperature for 1 hour after this operation.

The reaction product was treated in the same manner as that described in the previous Examples.

In this manner, di-n-propylacetonitrile was obtained in a yield of 56.4%.

EXAMPLE 9

Preparation of di-n-propylacetonitrile from valeronitrile (a) Preparation of the complex base lithium diethylamide/lithium amylate in a 2:1 ratio A solution of 6.15 g (0.07 mol) of t-amyl alcohol in 30 ml of tetrahydrofuran was introduced into 160 ml of a suspension of 15%-lithium diethylamide in hexane (0.21 mol). The mixture was heated for 2 hours at 55° C. When the reaction was terminated, the complex base was in the form of a solution.

(b) Formation of the carbanion of valeronitrile and alkylation with n-propyl bromide The method described in paragraph (b) of Example 8 above was employed using the same quantities of n-propyl bromide and valeronitrile i.e. 0.1 mol. The reaction product was treated in the same manner as that described in the previous Examples.

In this manner, di-n-propylacetonitrile was obtained in a yield of 35%.

EXAMPLE 10

Preparation of di-n-propylacetonitrile from valeronitrile (a) Preparation of the complex base sodium amide/sodium t-butylate in a 2:1 ratio The method of paragraph (a) of Example 2 above was employed using the same quantities of reagents but replacing isopropanol by 10.4 g (0.14 mol) of t-butanol and a mixture of 30 ml of benzene and 30 ml of tetrahydrofuran as solvents.

(b) Formation of the carbanion of valeronitrile and alkylation with n-propyl bromide The method of paragraph (b) of Example 2 above was employed but using 65 ml of benzene and 65 ml of tetrahydrofuran at a temperature between 14° and 18° C. The medium was maintained for a further 60 min. at 15° C. after the operation of addition was terminated. The product was isolated in accordance with the method used in the previous Examples.

In this manner, di-n-propylacetonitrile was obtained in a yield of 41.5%

EXAMPLE 11

Preparation of di-n-propylacetonitrile from valeronitrile (a) Preparation of the complex base sodium amide/sodium t-amylate in a 2:1 ratio The method of paragraph (a) of Example 2 above was employed but using 12.3 g (0.14 mol) of t-amyl alcohol in 30 ml of benzene in place of isopropanol and 16.4 g (0.42 mol) of sodium amide in 30 ml of benzene.

(b) Formation of the carbanion of valeronitrile and alkylation with n-propyl bromide The method of paragraph (b) of Example 2 was employed using the same quantities of valeronitrile and n-propyl bromide in 160 ml of benzene. To the complex base, 34 ml of hexamethylphosphorotriamide was added and the mixture so obtained was introduced into the reaction medium at a temperature between 5° and 13° C.

Stirring was maintained at this temperature for a further 2 hours after the operation of addition was terminated and the medium was treated in the same way as that described in the previous Examples.

In this manner, di-n-propylacetonitrile was obtained in a yield of 36.6%.

EXAMPLE 12

Preparation of di-n-propylacetonitrile from valeronitrile (a) Preparation of the complex base sodium amide/sodium t-amylate in a 2:1 ratio The method of paragraph (a) of Example 2 was employed but from 12.3 g (0.14 mol) of t-amyl alcohol in lieu of isopropanol and using 70 ml of tetrahydrofuran as diluent.

(b) Formation of the carbanion of valeronitrile and alkylation with n-propyl bromide The method of paragraph (b) of Example 2 was employed using the same quantities of n-propyl bromide and valeronitrile in 60 ml of tetrahydrofuran. The addition of the complex base to the reaction medium was effected at the reflux temperature of the mixture.

After the operation of addition was terminated, the temperature of the mixture was maintained at 72° C. for a further 2 hours. The reaction product was treated in the same way as that described in the previous Examples.

In this manner, di-n-propylacetonitrile was obtained in a yield of 52%.

EXAMPLE 13

Preparation of di-n-propylacetonitrile from valeronitrile (a) Preparation of the complex base sodium amide/sodium t-butylate in a 2:1 ratio The same method as in paragraph (a) of Example 2 above was employed using 4.87 g (0.125 mol) of sodium amide and 3.14 g (0.0425 mol) of t-butyl alcohol and 80 ml of tetrahydrofuran as diluent, while not exceeding a temperature of 25° C.

The mixture of complex base was not heated.

(b) Formation of the carbanion of valeronitrile and alkylation with n-propyl bromide In 70 ml of tetrahydrofuran, 8.3 g (0.1 mol) of valeronitrile and 12.3 g (0.1 mol) of n-propyl bromide was dissolved. The medium prepared in paragraph (a) hereabove was cooled to 1° C. and then the solution of valeronitrile and n-propyl bromide was introduced into the mixture of complex base. The rate of addition was such that the temperature did not exceed 4° C. The operation of addition lasted 45 minutes.

The temperature was allowed to return to about 20° C. in 1 hour and hydrolysis was carried out in the same manner as that described in the previous Examples.

In this manner, di-n-propylacetonitrile was obtained in a yield of 51%.

EXAMPLE 14

Preparation of 2-n-propyl-tetradecanenitrile from valeronitrile (a) Preparation of the complex base sodium amide/sodium t-amylate in a 2:1 ratio The method of paragraph (a) of Example 2 was employed but from 16.4 g (0.42 mol) of sodium amide and 12.3 g (0.14 mol) of t-amyl alcohol and using 70 ml of tetrahydrofuran as diluent.

(b) Formation of the carbanion of valeronitrile and alkylation with 1-chloro-dodecane The method of paragraph (b) of Example 2 was employed but using 16.6 g (0.2 mol) of valeronitrile and 40.95 g (0.2 mol) of 1-chloro-dodecane in 60 ml of tetrahydrofuran.

In this manner, 2-n-propyl-tetradecanenitrile was obtained in a yield of 24.6%.

EXAMPLE 15

Preparation of α-n-propyl-α-cyclohexyl-acetonitrile from valeronitrile (a) Preparation of the complex base sodium amide/sodium t-amylate in a 2:1 ratio The same method as in paragraph (a) of Example 14 was employed using the same quantities of reagents and diluent.

(b) Formation of the carbanion of valeronitrile and alkylation with cyclohexyl chloride The method of paragraph (b) of Example 2 was employed but using 16.6 g (0.2 mol) of valeronitrile and 23.7 g (0.2 mol) of cyclohexyl chloride in 60 ml of tetrahydrofuran.

In this manner, α-n-propyl-α-cyclohexyl-acetonitrile in a yield of 26.3% was obtained.

EXAMPLE 16

Preparation of α-n-propyl-α-benzyl-acetonitrile from valeronitrile (a) Preparation of the complex base sodium amide/sodium t-amylate in a 2:1 ratio The same method as in paragraph (a) of Example 14 was employed using the same quantities of reagents and diluent.

(b) Formation of the carbanion of valeronitrile and alkylation with benzyl chloride The method of paragraph (b) of Example 2 was employed but using 16.6 g (0.2 mol) of valeronitrile and 25.3 g (0.2 mol) of benzyl chloride in 60 ml of tetrahydrofuran.

In this manner, 2-n-propyl-α-benzyl-acetonitrile was obtained in a yield of 52.8%.

EXAMPLE 17

Preparation of 4-methyl-2-n-propyl-pentanenitrile from valeronitrile (a) Preparation of the complex base sodium amide/sodium t-amylate in a 2:1 ratio The method of paragraph (a) of Example 14 was employed using the same quantities of reagents and diluent.

(b) Formation of the carbanion of valeronitrile and alkylation with isobutyl bromide The same method as in paragraph (b) of Example 2 was employed but using 16.6 g (0.2 mol) of valeronitrile and 27.4 g (0.2 mol) of isobutyl bromide.

In this manner, 4-methyl-2-n-propyl-pentanenitrile was obtained in a yield of 63%.

EXAMPLE 18

Preparation of di-n-propylacetonitrile from acetonitrile (a) Preparation of the complex base sodium amide/sodium t-butylate in a 2:1 ratio The method described in paragraph (a) of Example 1 was employed from 164 g (4.2 mols) of sodium amide in 500 ml of tetrahydrofuran and 103.6 g (1.4 mol) of t-butanol in 700 ml of tetrahydrofuran.

(b) Formation of the carbanion of acetonitrile and alkylation with n-propyl bromide The method described in paragraph (b) of Example 1 was employed. The reaction was undertaken with a mixture of 41 g (1 mol) of acetonitrile and 246 g (2 mols) of n-propyl bromide dissolved in 600 ml of tetrahydrofuran, the mixture being cooled to 0° C. The operation of adding the suspension of complex base lasted 90 to 120 minutes, the temperature of the mixture being maintained between 0° and +5° C. during this operation. The temperature was then allowed to return to 10° C. and the mixture was maintained at this temperature for 1 hour under stirring and under nitrogen atmosphere.

The medium was hydrolysed by slowly pouring it while stirring into a mixture of 400 ml of water and 400 ml of ethyl ether. The aqueous phase was decanted and the organic solution was concentrated under vacuum.

In this manner, di-n-propylacetonitrile was obtained in a yield of 83.7%.

EXAMPLE 19

Preparation of di-n-propylacetonitrile from acetonitrile (a) Preparation of the complex base sodium amide/sodium t-butylate in a 2:1 ratio The method of paragraph (a) of Example 2 was employed but using 8.2 g (0.21 mol) of sodium amide and 5.2 g (0.07 mol) of t-butanol in 80 ml of tetrahydrofuran.

(b) Formation of the carbanion of acetonitrile and alkylation with n-propyl bromide The method described in paragraph (b) of Example 13 was employed but using 4.1 g (0.1 mol) of acetonitrile and 24.6 g (0.2 mol) of n-propyl bromide dissolved in 70 ml of tetrahydrofuran. The mixture of complex base was cooled to −10° C. and then slowly treated with a mixture of acetonitrile and n-propyl bromide at this temperature for 40 minutes. The medium was then treated in the same way as that described in the previous Examples.

In this manner, di-n-propylacetonitrile was obtained in a yield of 62.8%.

EXAMPLE 20

Preparation of dibenzylacetonitrile from acetonitrile (a) Preparation of the complex base sodium amide/sodium t-amylate in a 2:1 ratio The same method as in paragraph (a) of Example 14 was employed using the same quantities of reagents and diluent.

(b) Formation of the carbanion of acetonitrile and alkylation with benzyl chloride The method described in paragraph (b) of Example 18 was employed except that the reaction was carried out from 4.1 g (0.1 mol) of acetonitrile and 25.3 g (0.2 mol) of benzyl chloride dissolved in 30 ml of tetrahydrofuran.

In this manner, dibenzylacetonitrile was obtained in a yield of 75.3%.

EXAMPLE 21

Preparation of diisobutylacetonitrile from acetonitrile (a) Preparation of the complex base sodium amide/sodium t-amylate The method of paragraph (a) of Example 14 was employed using the same quantities of reagents and diluent.

(b) Formation of the carbanion of acetonitrile and alkylation with isobutyl bromide The method described in paragraph (b) of Example 18 was employed except that the reaction was carried out from 4.1 g (0.1 mol) of acetonitrile and 27.4 g (0.2 mol) of isobutyl bromide in 30 ml of tetrahydrofuran.

In this manner, diisobutylacetonitrile was obtained in a yield of 45%.

EXAMPLE 22

Preparation of tri-n-propylacetonitrile from acetonitrile (a) Preparation of the complex base sodium amide/sodium t-butylate in a 2:1 ratio The method of paragraph (a) of Example 2 was employed using 17.55 g (0.45 mol) of sodium amide and 11.10 g (0.15 mol) of t-butanol in 40 ml of tetrahydrofuran.

(b) Formation of the carbanion of acetonitrile and alkylation with n-propyl bromide To the mixture of complex base prepared in paragraph (a) was added a mixture of 4.1 g (0.1 mol) of acetonitrile and 40.59 g (0.33 mol) of n-propyl bromide. During this operation, which lasted 25 minutes, the temperature was maintained between 8° and 26° C. After the operation of addition was terminated, the mixture was maintained under stirring for a further 60 min. at room-temperature. The subsequent operations were the same as those described in the previous Examples.

In this manner, tri-n-propylacetonitrile was obtained in a yield of 66%.

EXAMPLE 23

Preparation of tri-n-propylacetonitrile from di-n-propylacetonitrile (a) Preparation of the complex base sodium amide/sodium t-butylate in a 2:1 ratio The same method as in paragraph (a) of Example 2 was employed but using 8.2 g (0.21 mol) of sodium amide and 5.2 g (0.07 mol) of t-butanol in 100 ml of tetrahydrofuran.

(b) Formation of the carbanion of di-n-propylacetonitrile and alkylation with n-propyl bromide To the mixture of complex base prepared in paragraph (a) hereabove, maintained at 20° C.±2°, a mixture of 12.5 g (0.1 mol) of di-n-propylacetonitrile and 16 g (0.13 mol) of n-propyl bromide was added. This operation lasted 5 minutes.

The mixture was stirred and the temperature maintained between 20° and 30° C. for 40 minutes. After that, the temperature was allowed to return slowly to 24° C. Hydrolysis was carried out as described in the following Examples.

In this manner, tri-n-propylacetonitrile was obtained in a yield of 94.5%.

EXAMPLE 24

Preparation of di-n-propylacetic acid from acetic acid (a) Preparation of the complex base sodium amide/sodium t-butylate in a 2:1 ratio In a flask maintained under nitrogen atmosphere 23.4 g (0.6 mol) of sodium amide was suspended in 60 ml of tetrahydrofuran. After that, a solution of 14.8 g (0.2 mol) of t-butanol in 10 ml of tetrahydrofuran was added to the medium. The temperature rose to 55° C.

The medium was maintained at this temperature for 90 min. and then allowed to return to room-temperature.

(b) Formation of the carbanion of acetic acid and alkylation with n-propyl bromide Into a flask maintained under nitrogen atmosphere, 4.8 g (0.1 mol) of 50%-sodium hyride in mineral oil and 60 ml of tetrahydrofuran were introduced. After that, 6 g (0.1 mol) of acetic acid in 10 ml of tetrahydrofuran were added drop-by-drop. The temperature rose to 55°-60° C. The sodium acetate obtained in gel form was maintained under stirring for 2 hours. After that, the complex base prepared under paragraph (a) hereabove was added at 20° C. and in one operation. The mixture was heated to 50° C. for 1 hour and then 24.6 g (0.2 mol) of n-propyl bromide were introduced into the mixture kept at 50°-55° C. After the operation of introduction was terminated, the temperature reached 60° C. The temperature of the medium was then maintained for 1 hour at 55° C. After that, the mixture was maintained for 8 hours at 20° C.

The mixture was hydrolysed by adding water and the aqueous phase was decanted. This phase was acidified by adding an aqueous solution of concentrated hydrochloric acid and then the medium was extracted several times with ethyl ether. The ethereal phase was washed with water, dried and the ether was evaporated off.

In this manner, a mixture was obtained which comprised 18.6% of di-n-propylacetic acid and 45% of valeric acid.

EXAMPLE 25

Preparation of di-n-propylacetic acid from valeric acid (a) Preparation of the complex base sodium amide/sodium t-butylate in a 2:1 ratio The same method as in paragraph (a) of Example 21 was employed using 11.7 g (0.3 mol) of sodium amide and 7.4 g (0.1 mol) of t-butanol in 80 ml of tetrahydrofuran.

(b) Formation of the carbanion of valeric acid and alkylation with n-propyl bromide Sodium valerate was prepared in accordance with the process of paragraph (b) of Example 21 with respect to sodium acetate but using 4.8 g (0.1 mol) of 50%-sodium hydride in mineral oil, 60 ml of tetrahyrofuran and 10.2 g (0.1 mol) of valeric acid. After that, 18.45 g (0.15 mol) of n-propyl bromide were introduced and the medium was heated at 60° C. under nitrogen atmosphere. To this mixture maintained under stirring the complex base was slowly added in 80 minutes.

The dropping-funnel was rinsed with 20 ml of tetrahydrofuran. The medium was maintained for a further 90 min. at 60° C. and allowed to stand for 8 hours at 20° C. After hydrolysis, the subsequent operations were the same as those referred to in paragraph (b) of Example 21.

In this manner, a mixture was obtained in a quantitative yield, this mixture comprising 83.3% of valeric acid and 16.7% of di-n-propylacetic acid.

EXAMPLE 26

Preparation of di-n-propylacetic acid from valeric acid (a) Preparation of the complex base lithium amide/lithium t-amylate in a 2:1 ratio Lithium amide was prepared by dissolving at −40° to −45° C. 1 g (0.15 mol) of lithium in 200 ml of liquid ammonia in the presence of a few crystals of ferric nitrate as catalyst. After the reaction was terminated, the ammonia was eliminated and, under nitrogen atmosphere, the complex base was prepared by introducing into the medium, 8.8 g (0.1 mol) of t-amyl alcohol in 30 ml of tetrahydrofuran. The mixture was heated for 2 hours at 55°–60° C.

(b) Formation of the carbanion of valeric acid and alkylation with n-propyl bromide Under nitrogen atmosphere, lithium valerate was prepared by introducing 33 ml (0.055 mol) of a 15%-solution of butyllithium in hexane into a solution of 5.1 g (0.05 mol) of valeric acid in 30 ml of tetrahydrofuran. The mixture was heated at 60° C. for 1 hour. The complex base was then introduced into the suspension of lithium valerate and the mixture was then heated for 1 hour at 60° C. After that 9.25 g (0.075 mol) of n-propyl bromide were added in 1 hour and the mixture was heated at 60° C. for 90 minutes. The mixture was then treated as indicated at the end of paragraph (b) of Example 21.

In this manner, a mixture was obtained in a yield of 72.5%, this mixture comprising 21.5% of di-n-propylacetic acid and 51% of valeric acid.

EXAMPLE 27

Preparation of di-n-propylacetic acid from valeric acid (a) Preparation of the complex base lithium diethylamide/lithium t-butylate in a 2:1 ratio To a mixture of 13.2 g (0.15 mol) of t-butanol and 21.9 g (0.3 mol) of diethylamide in 54 ml of benzene and 54 ml of hexamethylphosphorotriamide were added 3.2 g (0.46 mol) of lithium. The reaction mixture was maintained under stirring for 5 hours between 25° and 30° C.

(b) Formation of the carbanion of valeric acid and alkylation with n-propyl bromide Lithium valerate was prepared in tetrahydrofuran as described in paragraph (b) of Example 26 except that the lithium valerate so obtained was isolated by evaporating off the tetrahydrofuran.

In a mixture of 90 ml of hexane and 90 ml of toluene, 16.2 g (0.15 mol) of lithium valerate were suspended. The mixture of complex base prepared in paragraph (a) hereabove was added to this medium while maintaining the temperature of the reaction medium at 20° C. After the operation of addition of the complex base was terminated, the temperature of the mixture was increased to 36° C. for 1 hour.

After that, 27.54 g (0.22 mol) of n-propyl bromide were added. The temperature of the medium increased to 50° C. The mixture was then maintained between 50° and 57° C. for 8 hours. After that, the medium was cooled to −5° C. and 100 ml of concentrated hydrochloric acid were introduced while the temperature was maintained below 0° C.

THe solvents were eliminated under reduced pressure at a temperature not exceeding 40° C. and the residue was diluted by adding 75 ml of water. The mixture was extracted 4 times with 250 ml of ethyl ether. The ethereal phases were collected and the ethereal solution was washed with water. This solution was dried on sodium sulfate and the ether was eliminated under reduced pressure.

In this manner, di-n-propylacetic acid was obtained in a yield of 35.8% and 50.7% of valeric acid were collected.

EXAMPLE 28

Preparation of t-butyl di-n-propylacetate from t-butyl valerate (a) Preparation of the complex base sodium amide/sodium t-amylate in a 2:1 ratio The method of paragraph (a) of Example 2 was employed but using 6 g (0.155 mol) of sodium amide in 25 ml of tetrahydrofuran and 3.1 g (0.035 ml) of t-amyl alcohol in 10 ml of tetrahydrofuran.

(b) Formation of the carbanion of t-butyl valerate and alkylation with n-propyl bromide The mixture prepared in paragraph (a) above was cooled to −10° C. and a solution of 7.9 g (0.05 mol) of t-butyl valerate in 10 ml of tetrahydrofuran was slowly added. Stirring was maintained for a further 60 min. at −10° C. after the operation of addition was terminated.

After that, 7.4 g (0.06 mol) of n-propyl bromide and 9 g (0.05 mol) of hexamethylphosphotriamide were added at −10° C.

The mixture was kept 1 hour under stirring at about −10° C. After hydrolysis by adding water, the ether was extracted. The ethereal phase was dried and the ether was evaporated off.

In this manner, t-butyl di-n-propylacetate was obtained in a yield of 49.5%.

EXAMPLE 29

Preparation of N,N-diethyl di-n-propylacetamide from N,N-diethyl valeramide (a) Preparation of the complex base sodium amide/sodium t-amylate in a 2:1 ratio The method of paragraph (a) Example 2 was employed but using 8.2 g (0.21 mol) of sodium amide and 6.16 g (0.07 mol) of t-amyl alcohol in 50 ml of tetrahydrofuran.

(b) Formation of the carbanion of N,N-diethylvaleramide and alkylation with n-propyl bromide A mixture of 15.7 g (0.1 mol) of N,N-diethylvaleramide and 12.3 g (0.1 mol) of n-propyl bromide in 20 ml of tetrahydrofuran was cooled to 2° C. The mixture of complex base was added to this medium, under stirring while ensuring that the temperature did not exceed 20° C.

Stirring was maintained for a further 90 min. at this temperature and hydrolysis was carried out in the same manner as that described in the foregoing Examples.

In this manner, N,N-diethyl di-n-propylacetamide was obtained in a yield of 27.75% and 46.75% of non-reacted N,N-diethyl valeramide was recovered.

EXAMPLE 30

Preparation of N,N-diethyl di-n-propylacetamide from N,N-diethylvaleramide (a) Preparation of the complex base sodium amide/sodium t-amylate in a 2:1 ratio The method of paragraph (a) of Example 28 was employed but using 5 ml of tetrahydrofuran.

(b) Formation of the carbanion of N,N-diethyl valeramide and alkylation with n-propyl bromide Under nitrogen atmosphere the mixture of complex base was added drop-by-drop to a solution of 15.7 g (0.1 mol) N,N-diethyl valeramide in 15 ml of isopropyl ether at 20° C. The mixture was stirred at room-temperature for 1 hour and then 12.3 g (0.1 mol) of n-propyl bromide dissolved in 15 ml of isopropyl ether were introduced.

Stirring was maintained for 45 minutes and the medium was hydrolysed. The same method as that described in the foregoing Examples was used for isolating the desired product.

In this manner, N,N-diethyl di-n-propylacetamide was obtained in a yield of 34.9% and 55% of non-reacted N,N-diethyl valeramide was recovered.

EXAMPLE 31

Preparation of valeronitrile from acetonitrile (a) Preparation of the complex base sodium amide/sodium 2-ethoxy-ethylate Into a perfectly dry 500 ml-flask, 62.5 g of sodium amide and 145 g (200 ml) of diisopropyl ether were introduced.

At room-temperature, under stirring and under nitrogen atmosphere, a solution of 48.02 g of 2-ethoxyethanol and 72.5 g (100 ml) of diisopropyl ether was added drop-by-drop while maintaining the reaction medium at 45°–50° C.

The medium was maintained under stirring and inert atmosphere for a further 3 hours at 60° C. and then for 8 hours at room-temperature.

(b) Formation of the carbanion of acetonitrile and alkylation with n-propyl bromide Into a 1 l-flask, perfectly dry, were introduced 53.3 g of acetonitrile, 123.0 g of n-propyl bromide and 289.5 g (400 ml) of diisopropyl ether. The medium was stirred at room-temperature and kept under nitrogen atmosphere. The suspension of complex base was transferred into a 500 ml dropping-funnel and maintained under stirring. The flask which had contained the complex base was rinsed with 72.5 g (100 ml) of diisopropyl ether and this ether was added to the content of the dropping-funnel. The suspension of complex base was then introduced, by fractions, into the reaction medium while the inner temperature was maintained between 30° and 35° C. This operation lasted 30 minutes.

The medium was then allowed to stand for 30 minutes and subsequently cooled to 0° to 5° C. After hydrolysis at this temperature by progressively adding 160 g of distilled water, the aqueous phase was allowed to decant for 15 minutes. The organic phase was successively washed with 65 g of distilled water, 47 g of 36%-hydrochloric acid and 3 fractions, each of 125 g of distilled water. The organic phase was dried on sodium sulfate and the solvent was evaporated at atmospheric pressure to reach 73°±1° C. at the head of the column.

In this manner, 63.5 g of a crude oil was isolated titrating 88.2% in desired product.

Yield in valeronitrile: 67.5%.

Using the same method as that described, the following compounds were prepared from the appropriate products:

Compounds

Hydrocinnamonitrile from benzyl bromide.

The crude product obtained titrated 62.1% in desired product.

Yield: 64.8%.

Isocapronitrile from isobutyl bromide.

The crude product obtained titrated 81.3% in desired product.

Yield: 35.5%.

4-Pentenonitrile from allyl bromide.

The crude product obtained titrated 58% in desired product.

Yield: 53.7%.

EXAMPLE 32

Preparation of diisobutylacetonitrile from acetonitrile (a) Preparation of the complex base sodium amide/sodium 2-ethoxy-ethylate The same method as in paragraph (a) of Example 30 was employed but using 66.3 g of sodium amide in 181 g (250 ml) of diisopropyl ether and 51 g of 2-ethoxyethanol in 54.5 g (75 ml) of diisopropyl ether.

(b) Formation of the carbanion of acetonitrile and alkylation with isobutyl bromide Into a flask, 20.5 g of acetonitrile, 137 g of isobutyl bromide and 325.5 g (450 ml) of diisopropyl ether were introduced. The reaction was carried out at 30° C.±2° and the introduction of the complex base lasted 40 min. The working conditions as well as the isolation procedure were the same as described in paragraph (b) of Example 30.

In this manner, 59.75 g of a crude oil were isolated titrating 76.4% in desired product.

Yield in diisobutylacetonitrile: 60%.

Using the same method as that described above diallylacetonitrile was prepared from allyl bromide. The crude product obtained titrated 39.2%.

Yield in diallylacetonitrile: 30.7%.

EXAMPLE 32 A

Preparation of dibenzylacetonitrile from acetonitrile (a) Preparation of the complex base sodium amide/sodium t-amylate Into a 500 ml-flask, perfectly dry, were introduced 81.9 g (2.1 mols) of sodium amide in powder and 88.8 g (100 ml) of dry tetrahydrofuran. At room-temperature, under stirring and under nitrogen atmosphere, a solution of 61.6 g (0.7 mol) of t-amyl alcohol and 44.4 g (50 ml) of dry tetrahydrofuran was added drop-by-drop while the temperature was maintained between 45°–50° C. The medium was kept at 60° C. for 90 min. and then for 1 hour at room-temperature.

(b) Formation of the carbanion of acetonitrile and alkylation with benzyl chloride Into a 1-l flask, prefectly dry, were introduced 20.5 g (0.5 mol) of dry acetonitrile, 126.5 g (1 mol) of benzyl chloride and 266.4 g (300 ml) of dry tetrahydrofuran.

The medium was stirred under nitrogen atmosphere while maintaining the inner temperature at 10°/15° C. during the operation of introduction of the suspension of complex base.

This operation lasted 90 minutes. The medium was maintained at 15° C. for 1 hour after the operation of introduction and hydrolysed at a temperature below 15° C. by addition of a mixture of 400 g of distilled water and 285.6 g (400 ml) of ethyl ether. The aqueous phase was decanted and the organic phase was successively washed with a solution of 70 g of water and 50 g of 36%-hydrochloric acid and then with 3 fractions, each of 120 g, of water. The medium was dried on sodium sulphate and the solvent was eliminated under atmospheric pressure to 80° C. at the head of the column.

In this manner 115 g of a crude oil was obtained titrating 63.6% in desired product.

Yield in dibenzylacetonitrile: 66.2%.

EXAMPLE 33

Preparation of 2-ethyl-valeronitrile from valeronitrile (a) Preparation of the complex base sodium amide/sodium 2-ethoxy-ethylate The method described in paragraph (a) of Example 31 was employed.

(b) Formation of the carbanion of valeronitrile and alkylation with ethyl bromide The method described in paragraph (b) of Example 31 was employed except that the alkylation was performed between 28° and 30° C. and the reaction medium maintained for 1 hour at room-temperature before hydrolysis. In this manner, 114 g of crude oil was obtained titrating 77.7% in desired product.

Yield in 2-ethyl-valeronitrile: 80%.

Following the same procedure, the following compounds were prepared taking into account the alterations indicated:

Compounds

2-Allyl-valeronitrile.

Duration of the operation of addition of the complex base: 40 min.

Temperature of alkylation: 30° to 35° C.

The crude oil obtained titrated 60.8% in desired product.

Yield: 61.3%.

2-Isobutyl-valeronitrile.

Duration of the operation of addition of the complex base: 27 min.

Temperature of alkylation: 35° to 38° C.

The crude oil obtained titrated 97.3% in desired product.

Yield: 72.7%.

B.P.: 190° C. or 99°–101° C. under 20 mm Hg.

$n_D^{20} = 1.4199$.

I.R. Spectrum: C≡N at ≃2245 cm$^{-1}$.

2-Benzyl-valeronitrile.

Duration of the operation of addition of the complex base: 45 min.

Temperature of alkylation: 30° to 35° C.

The crude oil obtained titrated 98.9% in desired product.

Yield: 62.5%.

B.P.: 85°–86° C. under 0.2 mm Hg.

$n_D^{20} = 1.5048$.

I.R. spectrum: C≡N at ≃2245 cm$^{-1}$.

2-Dodecyl-valeronitrile.

Duration of the operation of addition of the complex base: 20 min.

Temperature of alkylation: 45° to 50° C.

The crude oil obtained titrated 99.5% in desired product.

Yield: 52.4%.

B.P.: 140° C. under 0.4 mm Hg or 127° C. under 0.15 mm Hg.

$n_D^{24} = 1.4425$.

I.R. Spectrum: C≡N at ≃2245 cm$^{-1}$ and 2195 cm$^{-1}$.

2-Propargyl-valeronitrile.

Duration of the operation of addition of the complex base: 30 min.

Temperature of alkylation: 30° to 35° C.

The crude oil obtained titrated 34.5% in desired product.

Yield: 31.2%.

I.R. Spectrum (film): ≡CH at 3280 cm$^{-1}$; C≡N at 2240 cm$^{-1}$; C≡C at 2120 cm$^{-1}$.

$n_D^{20} = 1.4152$.

EXAMPLE 34

Preparation of α-benzyl di-n-propylacetonitrile from di-n-propylacetonitrile (a) Preparation of the complex base sodium amide/sodium 2-ethoxy-ethylate Into a 250-ml flask, perfectly dry, were introduced 8.2 g of sodium amide and 66.6 g (75 ml) of tetrahydrofuran. At room-temperature, under stirring and under nitrogen atmosphere, a solution of 6.3 g of 2-ethoxy-ethanol in 22.2 g (25 ml) of tetrahydrofuran was added drop-by-drop while maintaining the temperature between 40° and 45° C. The medium was heated to 55°/60° C. and this temperature was maintained for 2 hours. After that the mixture was cooled to room-temperature.

(b) Formation of the carbanion of di-n-propylacetonitrile and alkylation with benzyl chloride To the suspension of complex base obtained in paragraph (a) hereabove was added, in 5 minutes, a mixture of 16.5 g of benzyl chloride and 12.5 g of di-n-propylacetonitrile.

The reaction was exothermic and the exothermicity remained for about 45 min. after the operation of introduction was terminated. The mixture was then cooled to room-temperature and this temperature was maintained for 1 hour. After that, the mixture was cooled to 0° to 5° C. and then hydrolysed without exceeding 20° C. by adding 50 g of distilled water. After decantation, the solvent was eliminated under reduced pressure. The concentrate was then taken up in 107 g (150 ml) of ethyl ether. The ethereal phase was successively washed with 2 fractions, each of 25 g, of a 10% aqueous solution of hydrochloric acid and 3 fractions, each of 25 g, of distilled water. After drying on sodium sulphate, the ether was eliminated under atmospheric pressure and then under reduced pressure (residual pressure: ≃50 mm Hg).

In this manner, 24.6 g of a crude oil were isolated titrating 95.8% in desired product. This oil was then rectified under reduced pressure. Yield in α-benzyl di-n-propylacetonitrile: 75.9%.

B.P.: 108° C. under 0.5 mm Hg.
$n_D^{21} = 1.5071$.
I.R. Spectrum: C≡N at 2240 cm$^{-1}$.

Using the same method as that described above, the following compounds were prepared:

Compounds

α-Ethyl di-n-propylacetonitrile.
The crude oil titrated 99.3% in desired product.
Yield: 51.5%.
B.P.: 56° C. under 1.7 mm Hg or 49° C. under 0.8 mm Hg.
$n_D^{27} = 1.4288$.
I.R. Spectrum: —C≡N at 2240 cm$^{-1}$.

α-Allyl di-n-propylacetonitrile
The crude oil titrated 100% in desired product.
Yield: 61.5%:
B.P.: 74° C. under 1.6 mm Hg.
$n_D^{22} = 1.4419$.
I.R. Spectrum: C≡N at 2240 cm$^{-1}$.

α-Isobutyl di-n-propylacetonitrile.
The crude oil titrated 98.2% in desired product.
Yield: 62.5%.
B.P.: 74°–75° C. under 1.6 mm Hg.
$n_D^{21} = 1.4378$.
I.R. Spectrum: C≡N at 2240 cm$^{-1}$.

EXAMPLE 35

Preparation of di-n-propylacetonitrile from valeronitrile (the complex base is added to a nitrile/halide mixture-total quantity of solvent: 6.4 volumes)

(a) Preparation of the complex base sodium amide/sodium 2-ethoxy-ethylate

Into a 100 ml-flask equipped with a condenser, a magnetic stirrer, a thermometer, an isobaric dropping-funnel having a nitrogen inlet were introduced 12.9 g (0.3307 mol) of sodium amide and then 40 ml of toluene. The medium was stirred under nitrogen atmosphere. Through the dropping-funnel was further added a mixture of 9.9 g (0.110 mol) of 2-ethoxy-ethanol in 10 ml of toluene. The medium was brought to 60°–65° C. for 90 minutes and then stirred for 4 to 5 hours under nitrogen atmosphere.

(b) Formation of the carbanion of valeronitrile and alkylation with n-propyl bromide Into a 250 ml-flask fitted with a magnetic stirrer, a thermometer, a condenser and an isobaric dropping-funnel having a nitrogen inlet were introduced 16.6 g or 20.8 ml (0.2 mol) of valeronitrile, 24.6 g or 18.2 ml (0.2 mol) of n-propyl bromide and 90 ml of toluene. The complex base was then transferred to the isobaric dropping-funnel and the 100 ml-flask was rinsed with 10 ml of toluene. The total apparatus was then placed under nitrogen atmosphere and the complex base was stirred to obtain a homogeneous medium. The reaction medium was also placed under stirring, preheated at 35° C. and the suspension of complex base was added by fractions. The temperature gradually rose to 45° C. and was maintained at 45°±3° C. by means of a water-bath. The operation of addition took about 1 hour. Stirring was maintained for 30 minutes together with the nitrogen atmosphere and the medium was allowed to return to room-temperature. The reaction medium while still being maintained under nitrogen atmosphere was cooled to +5° to +10° C. and then slowly hydrolyzed by adding 40 to 50 ml of water. The organic layer was decanted out and successively washed with 60 ml of 20%-hydrochloric acid (in volume) and then with 4 fractions each of 60 ml of water. The organic layer was dried on sodium sulphate and filtered.

In this manner, di-n-propylacetonitrile was obtained in a yield of 83.82% together with 5.95% of valeronitrile and 2.47% of tri-n-propylacetonitrile.

Using the same procedure as that described above but with the variations indicated below di-n-propylacetonitrile was prepared with the following results:

| Solvent | Working conditions | | Yield in % | | |
|---|---|---|---|---|---|
| | T° of reaction (°C.) | Duration of op. of addition of the complex base (min.) | I(*) | II() | III(*) |
| Benzene (6.4 vol.) | 45 ± 3 | 30 | 8.22 | 82.45 | 2.4 |
| Cyclohexane (6.4 vol.) | 45 ± 3 | 45 | 1.66 | 85.14 | 2.68 |
| Diisopropyl ether (6.4 vol.) | 40–45 | 60 | 4.6 | 87.1 | 3 |

(*)I = valeronitrile
(**)II = di-n-propylacetonitrile
(***)III = tri-n-propylacetonitrile

EXAMPLE 36

Preparation of di-n-propylacetonitrile from valeronitrile (a nitrile/halide mixture is added to the complex base)

A. The complex base is suspended in the total quantity of solvent i.e. 6.4 volumes (a) Preparation of the complex base sodium amide/sodium 2-ethoxy-ethylate Into a 250 ml-flask equipped with a stirrer, a condenser, a thermometer and an isobaric dropping-funnel having a nitrogen inlet were introduced 12.9 g (0.3307 mol) of sodium amide and 100 ml of dry diisopropyl ether. The medium was stirred under nitrogen atmosphere and then 9.9 g (0.110 mol) of 2-ethoxy-ethanol in 60 ml of diisopropyl ether were added. The medium was heated to 60° C. for 90 minutes and stirring was maintained at room-temperature for 4 to 5 hours.

(b) Formation of the carbanion of valeronitrile and alkylation with n-propyl bromide To the suspension of complex base so obtained, a mixture of 16.6 g or 20.8 ml (0.2 mol) of valeronitrile and 24.6 g or 18.2 ml (0.2 mol) of n-propyl bromide was added, drop-by-drop, so as to ensure a reaction temperature of 20° to 25° C. which was maintained by means of a water-bath (about 10° C.). The operation of addition took 25 minutes. The medium was stirred at 25° C. for a further 30 minutes under nitrogen atmosphere and then cooled to +5° C. After slow hydrolysis with 50 ml of water, the mixture was decanted and washed successively with 60 ml of 20%-hydrochloric acid (in volume) and then with 4 fractions each of 60 ml of distilled water. After drying the organic phase was concentrated under atmospheric pressure.

In this manner, 23.9 g of crude di-n-propylacetonitrile were obtained. Di-n-propylacetonitrile was thus provided in a yield of 78.2% together with 8.8% of valeronitrile and 5.7% of tri-n-propylacetonitrile.

Using the same procedure as that described above but with the variations indicated below di-n-propylacetonitrile was prepared with the following results:

| Solvent | Working conditions | | Yield in % | | |
|---|---|---|---|---|---|
| | T° of reaction (°C.) | Duration of op. of addition of the complex base (min.) | I(*) | II() | III(*) |
| Toluene (6.4 vol.) | 30–35 | 20 | 6.6 | 79.65 | 3.75 |
| Benzene (5.6 vol.) | 30–35 | 20 | 13 | 71.8 | 4.8 |
| Cyclohexane (6.4 vol.) | 28–30 | 10 | 13.3 | 76 | 2.8 |
| Benzene (4.8 vol.) | 30–35 | 32 | 7.6 | 78.8 | 6 |

(*)I = valeronitrile
(**)II = di-n-propylacetonitrile
(***)III = tri-n-propylacetonitrile B. The nitrile is in 3 volumes of solvent and the complex base in 3.6 volumes of solvent (a) Preparation of the complex base sodium amide/sodium 2-ethoxy-ethylate In a 250 ml-flask equipped with a stirrer, a condenser, a thermometer and an isobaric dropping-funnel having a nitrogen inlet were placed 12.9 g (0.3307 mol) of sodium amide and then 60 ml of diisopropyl ether. The mixture was stirred under nitrogen atmosphere and 9.9 g (0.110 mol) of 2-ethoxyethanol diluted in 15 ml of diisopropyl ether were added drop-by-drop. The medium was brought to 60° C. for 90 minutes and then stirred for 5 hours at room-temperature. After that 15 ml of diisopropyl ether were added.

(b) Formation of the carbanion of valeronitrile and alkylation with n-propyl bromide To the complex base so obtained, was added at 25° C. a mixture of 16.6 g (0.2 mol) of valeronitrile and 24.6 g (0.2 mol) of n-propyl bromide in 75 ml of diisopropyl ether. This operation of addition took 25 minutes at 30°±2° C., this temperature being maintained by means of a wather-bath.

The medium was then stirred at 30° C. for 30 minutes, cooled to 5° C. and slowly hydrolyzed with 50 ml of water. After decantation the medium was washed with 60 ml of 20%-hydrochloric acid and then with 4 fractions each of 60 ml of water. The organic phase was dried and then concentrated at atmospheric pressure.

In this manner, 29.9 g of crude di-n-propylacetonitrile was obtained.

Di-n-propylaceonitrile was thus provided in a yield of 74.75% together with 9% of valeronitrile and 6.44% of tri-n-propylacetonitrile.

Using the same procedure as that described above but with the variations indicated below di-n-propylacetonitrile was prepared with the following results:

| Solvent | Working conditions | | Yield in % | | |
|---|---|---|---|---|---|
| | T° of reaction (°C.) | Duration of op. of addition of the complex base (min.) | I(*) | II() | III(*) |
| Toluene (6.6 vol.) | 30–35 | 30 | 12.2 | 70.6 | 1.82 |

EXAMPLE 37

Preparation of di-n-propylacetonitrile from acetonitrile

A. Addition of the complex base to an acetonitrile/n-propylbromide mixture-total quantity of solvent: 10.8 volumes (a) Preparation of the complex base sodium amide/sodium 2-ethoxy-ethanol Into a 100 ml-flask fitted with a condenser, a magnetic stirrer, a thermometer and an isobaric dropping-funnel having a nitrogen inlet were introduced 12.9 g (0.3307 mol) of sodium amide and 40 ml of toluene. The mixture was stirred under nitrogen atmosphere and a solution of 9.9 g (0.110 mol) of 2-ethoxy-ethanol in 20 ml of toluene was added. The medium was then brought to 60°–65° C. for 90 min. and maintained under stirring and nitrogen atmosphere for 4 to 5 hours.

(b) Formation of the carbanion of acetonitrile and alkylation with n-propyl bromide In a 250 ml-flask fitted with a condenser, a stirrer, a thermometer, an isobaric dropping-funnel having a nitrogen inlet were placed 4.1 g (0.1 mol) of dry acetonitrile, 24.6 g (0.2 mol) of n-propyl bromide and 85 ml of toluene.

The complex base so obtained was transferred to the isobaric dropping-funnel and the 100 ml-flask was rinsed with 15 ml of toluene. The total apparatus was then placed under nitrogen atmosphere and the complex base was stirred so as to obtain an homogeneous medium. The reaction mixture was then stirred and pre-heated to 35° C. After that, the suspension of complex base was added by fractions while the temperature was maintained between 40° and 45° C. by means of an iced water-bath. The operation of addition took 22 minutes and then the temperature was maintained at 45° C. The reaction medium was then allowed to return to room-temperature and stirring was maintained for 30 minutes. After cooling to +5° C. under nitrogen atmosphere the medium was slowly hydrolysed with 40 to 50 ml of water. The mixture was decanted and the organic phase was washed with 60 ml of 20%-hydrochloric acid (in volume) and then with 4 fractions each of 60 ml of water. The organic layer was dried on sodium sulphate and filtered.

In this manner, di-n-propylacetonitrile was obtained in a yield of 65.9% together with 25.9% of valeronitrile and 3% of tri-n-propylaceonitrile. Using the same procedure as that described above but with the variations indicated below di-n-propylaceonitrile was prepared with the following results:

| Solvent | Working conditions | | Yield in % | | |
| --- | --- | --- | --- | --- | --- |
| | T° of reaction (°C.) | Duration of op. of addition of the complex base (min.) | I(*) | II() | III(*) |
| Diisopropyl ether (10.8 vol.) | 35 | 60 | 21.5 | 56.8 | 2.1 |
| Cyclohexane (12.8 vol) | 40 ± 2 | 55 | — | 50.5 | 10 |

B. Addition of an acetonitrile/n-propyl bromide mixture to the complex base-total quantity of solvent: 18.6 volumes (a) Preparation of the complex base sodium amide/sodium 2-ethoxy-ethylate Into a 250 ml-flask fitted with a condenser, a magnetic stirrer, a thermometer and an isobaric dropping-funnel having a nitrogen inlet were introduced 12.9 g of sodium amide and 100 ml of diisopropyl ether. The mixture was stirred under nitrogen atmosphere and a solution of 9.9 g (0.110 mol) of 2-ethoxy-ethanol in 60 ml of diisopropyl ether was added. The medium was then brought to 60° C. for 90 minutes and maintained under stirring and nitrogen atmosphere for a further 4 to 5 hours.

(b) Formation of the carbanion of acetonitrile and alkylation with n-propyl bromide The complex base previously obtained was cooled to 15° C. and a solution of 4.1 g (0.1 mol) of acetonitrile and 24.6 g (0.2 mol) of n-propyl bromide was rapidly added through the dropping-funnel. This operation of addition took 10 minutes at 15° to 26° C., this temperature being maintained by means of a water-bath. The dropping-funnel was rinsed with 10 ml of diisopropyl ether and the reaction medium was stirred for 20 minutes at 25° C. After cooling to +5° C., the mixture was slowly hydrolysed using 50 ml of water and decanted. The organic layer was successively washed with 60 ml of 20%-hydrochloric acid (in volume) and then with 4 fractions each of 60 ml of distilled water. After drying on sodium sulphate the organic phase was concentrated under atmospheric pressure.

In this manner, 11.75 g of crude di-n-propylaceonitrile was obtained. Di-n-propylacetonitrile was thus provided in a yield of 65.2% together with 16% of valeronitrile and 7.3% of tri-n-propylaceonitrile.

Using the same procedure as that described above but with the variations indicated below di-n-propylacetonitrile was prepared with the following results:

| Solvent | Working conditions | | Yield in % | | |
| --- | --- | --- | --- | --- | --- |
| | T° of reaction (°C.) | Duration of op. of addition of the complex base (min.) | I(*) | II() | III(*) |
| Toluene (8 vol.) | 10-30 | 16 | 22 | 70.7 | 4.9 |

We claim:

1. Process for preparing a nitrile of general formula:

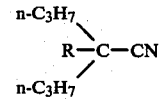
I in which R represents hydrogen or n-propyl, whereby n-propyl bromide and a nitrile of the formula:

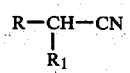
II in which R and $R_1$, which are the same or different, represent hydrogen or n-propyl, are placed in contact, both reactants being in the same anhydrous medium selected from benzene, toluene, cyclohexane, diisopropyl ether, tetrahydrofuran or a mixture of such solvents, at a temperature between −10° and +45° C., with a mixture composed of 2 parts of a sodium amide to 1 part of a sodium alcoholate, the latter being selected from sodium n-propylate, sodium isopropylate, sodium t-butylate and sodium 2-ethoxyethylate, and the resulting propylated nitrile separated from the reaction mixture.

2. Process according to claim 1 wherein the sodium amide/sodium alcoholate mixture is added to the n-propyl bromide and to the nitrile of formula II, both of the latter being in the anhydrous medium.

3. Process according to claim 1 wherein the n-propyl bromide and the nitrile of formula II, both of which are in the anhydrous medium, are added to the sodium amide/sodium alcoholate mixture.

4. Process according to claim 1 wherein the sodium alcoholate is sodium 2-ethoxyethylate.

5. Process according to claim 1 wherein the solvent is toluene.

6. Process according to claim 1 wherein the nitrile of formula II is acetonitrile and the nitrile of formula I is di-n-propylaceonitrile.

7. Process according to claim 1 wherein the nitrile of formula II is valeronitrile and the nitrile of formula I is di-n-propylacetonitrile.

8. Process according to claim 1 wherein the nitrile of formula II is di-n-propylacetonitrile and the nitrile of formula I is tri-n-propylaceonitrile.

* * * * *